US009839651B1

(12) United States Patent
Vakina et al.

(10) Patent No.: US 9,839,651 B1
(45) Date of Patent: *Dec. 12, 2017

(54) FOOD SUPPLEMENT FOR RESTORING MALE SEX DRIVE (LIBIDO)

(71) Applicant: Parapharm LLC, Penza (RU)

(72) Inventors: Tatiana N. Vakina, Penza (RU); Elena V. Petrova, Penza (RU); Viacheslav N. Trifonov, Penza (RU); Evgeny N. Krutiakov, Penza (RU); Aleksandr V. Fedorov, Penza (RU); Elena S. Andreyeva, Penza (RU); Tatiana V. Elistratova, Penza (RU); Irina V. Khomyakova, Penza (RU); Galina A. Tolbina, Penza (RU)

(*) Notice: Subject to any disclaimer, the term of this patent is extended or adjusted under 35 U.S.C. 154(b) by 0 days.

This patent is subject to a terminal disclaimer.

(21) Appl. No.: 15/673,405

(22) Filed: Aug. 9, 2017

Related U.S. Application Data

(63) Continuation-in-part of application No. 14/422,206, filed as application No. PCT/RU2013/000173 on Mar. 6, 2013, now Pat. No. 9,730,973.

(51) Int. Cl.
| A61K 36/00 | (2006.01) |
| A61K 33/30 | (2006.01) |
| A61K 31/198 | (2006.01) |
| A61K 31/7048 | (2006.01) |
| A61K 31/201 | (2006.01) |
| A61K 35/64 | (2015.01) |
| A61K 31/675 | (2006.01) |
| A61K 36/296 | (2006.01) |
| A61K 31/704 | (2006.01) |
| A61K 36/258 | (2006.01) |
| A61K 31/575 | (2006.01) |
| A61K 36/28 | (2006.01) |

(52) U.S. Cl.
CPC ............ *A61K 33/30* (2013.01); *A61K 31/198* (2013.01); *A61K 31/201* (2013.01); *A61K 31/575* (2013.01); *A61K 31/675* (2013.01); *A61K 31/704* (2013.01); *A61K 31/7048* (2013.01); *A61K 35/64* (2013.01); *A61K 36/258* (2013.01); *A61K 36/28* (2013.01); *A61K 36/296* (2013.01)

(58) Field of Classification Search
CPC ....................................................... A61K 36/00
See application file for complete search history.

*Primary Examiner* — Qiuwen Mi
(74) *Attorney, Agent, or Firm* — Alexander Rabinovich; Patentagar PLLC

(57) ABSTRACT

A food supplement for restoring male sex drive (libido) comprises in a daily dose a set of L-arginine, rutin from pollen or beebread, decenic acids from drone brood, zinc from a zinc compound, and vitamin $B_6$. It also comprises icariin from horny goat weed, saponins from true or false *ginseng* root, and ecdysteroids from *Leuzea* or crowned saw-wort, in various combinations thereof.

7 Claims, No Drawings

FOOD SUPPLEMENT FOR RESTORING MALE SEX DRIVE (LIBIDO)

CROSS-REFERENCE TO RELATED APPLICATIONS

The present application is a continuation-in-part of U.S. application Ser. No. 14/422,206 filed Feb. 18, 2015, pending, which is a U.S. National phase application of International application WO 2014/031026 filed Mar. 6, 2013 and claiming priority from Russian application 2012135560 filed Aug. 20, 2012, all three above applications being incorporated for reference into the present application in their entirety.

BACKGROUND OF THE INVENTION

1. Field of the Invention

The invention relates to biologically active food supplements to restore sex drive (libido) and improve sexual function in male and is based on natural ingredients.

2. Description of Related Art

Sexual dysfunction, including decreased libido, erectile and ejaculation dysfunction, as well as infertility, are widespread medical, psychological, and social problems.

Today, there exists quite a few pharmaceutical drugs—inhibitors of phosphodiesterase of type 5 (PDEI-5), such as Viagra, Cialis, Zidena, Levitra, for treating sexual dysfunctions. At the same time, the high cost of these drugs and significant risk of adverse drug reactions, especially in patients with cardiovascular disease, limit their widespread use. In addition, there are patients (15-42%) in which PDEI-5 are inefficient due to the mechanism of action of this group of drugs. It is known that these drugs can potentiate NO relaxing action on smooth muscle tissue of trabecular cells. However, the starting point for NO release from nerve endings is the impulses coming from the central nervous system. Their intensity depends on the patient's response to sexual stimuli, i.e. evidence of sex drive or libido. With a sharp decrease of libido (this is it that fades with age in the first place), monotherapy with PDES inhibitors is ineffective due to lack of substrate for their actions (Segraves K. B., Segraves R. T., *Hypoactive sexual desire disorder: prevalence and comorbidity in 906 subjects*, J Sex Marital Ther, 1991, Vol. 17, pp. 55-58; Pushkar D. Yu., Yudovsky S. O., *Combined use of Enerion (sulbutiamin) and Cialis (tadalafil) in therapy of patients with erectile dysfunction*, 2007—http://medi.ru/doc/a0210603.htm).

As far as androgen replacement therapy (ART) employing testosterone preparations used per os, intramuscularly, or percutaneously) is concerned, there left a number of unresolved problems despite the variety of dosage forms. Firstly, none of the drugs is able to precisely reproduce a circadian rhythm in the serum testosterone level. Secondly, a number of studies have shown that exogenous increase of testosterone has a greater influence on the erectile function rather than on sexual-erotic, libidinal component, this being caused by a visceral defect of hypothalamic brain structures. Thirdly, androgens are potentially able to have adverse effects not only due to cutting off its own mechanisms of androgen production but also due to affecting homeostasis maintaining systems suppressing the production of endogenous androsteroids. Side effects primarily affect the prostate gland, lipid profile, cardiovascular system, hematologic state, sleep system, social behavior, and emotional status (Pushkar' D. Yu., Segal A. S., Yudovsky S. O., *Current opportunities for androgen replacement therapy in cases of male hypogonadism*, Pharmaceutical Bulletin, 2008, No. 13, p. 33). When administering ART, one should ensure the functional safety of the liver to avoid final catabolism disorders with increased levels of estrogen that provokes release of inhibiting substances able to block achievable, albeit usually modest, positive therapeutic results.

Impaza—a preparation containing antibodies to human endothelial NO-synthase. The main mechanism of its action is to enhance the activity of endothelial NO-synthase, to recover production of nitric oxide (NO) by endothelium, and to increase the cGMP content in smooth muscles and to relax same that leads to a rising of blood supply to the corpus cavernosum. These effects primarily recover erection. With regard to libido, target studies have not been conducted; according to individual data, the increase of libido is less than 20% (Neumark A. I., Simashkevich A. V., Aliyev R. T., *Treating patients with prostate benign hyperplasia complicated by the erectile dysfunction*, Attending physician, 2010, No. 4, pp. 89-91).

The closest analogue to the proposed supplement are formulations that are useful in the treatment of male and female impotence; they are based on extracts of *Tribulus terrestris*, *Epimedium koreanum* and Cinnamon *cassia* combined in a specific weight ratio, and optionally contain arginine or physiologically equivalent ester, its salt or precursor and suitable carrier or excipient (patent of the Russian Federation No 2313358, 2003).

The effect of this composition on libido is low. It is primarily aimed at the elimination of erectile dysfunction. Another disadvantage of this composition is the use of a medicinal plant *Tribulus terrestris*, which is prohibited by Rospotrebnadzor (a Russian analog of the FDA) for using as a raw material for the production of biologically active additives to food because of the high toxicity of this plant.

Offered in this application is a food supplement to restore/enhance libido with the following daily dosage composition shown in ranges:

| Components | Mg of active substance |
| --- | --- |
| Saponins from true or false ginseng roots | from 5 mg to 20 mg |
| Ecdysteroids from Leuzea root | from 0.1 mg to 30 mg |
| L-Arginine | From 300 mg to 1,000 mg |
| Icariin from Horny goat weed | From 20 to 150 mg |
| Decenoic acids from male bee brood | from 0.4 mg to 1 mg |
| Rutin from pollen or beebread | from 40 mg to 100 mg |
| Zinc from zinc citrate | from 6 mg to 60 mg |
| Vitamin $B_6$ | from 0.3 mg to 3 mg, | the upper limit being selected due to toxicity, the lower limit—due to effectiveness.

L-Arginine is a protein-forming amino acid. It is a source of adequate forming of nitric oxide (NO) by vascular endothelium, which is associated with the dependent relaxation of smooth muscle cells of cavernous tissue determining the hemodynamic changes in the penis during erection and rigidity phase (K. E. Anderson, *Pharmacology of penile*

*erection*, Pharmacol. Rev., 2001, 53 (September (3): 417-50.). L-arginine has a stimulating effect on the reproductive system: it increases the production of seminal fluid and spermatogenesis; stimulates the potency and sexual activity; can increase the strength and duration of genitals blood filling; prolongs the duration of sexual intercourse; enhances pleasant sexual sensations; makes orgasms last longer; increases the frequency and intensity of orgasms. It improves mood, activity and endurance.

Horny Goat Weed contains icariin—flavonol derived from plants of *Epimedium* family, which are widely known as Horny Goat Weed (literally—an herb of a horny goat). The extract of *Epimedium* for centuries has been used in Chinese traditional medicine to treat impotence and improve sexual function.

The mechanism of its action is similar to a phosphodiesterase inhibitor. It increases the production of nitric oxide, improves circulation and myotrophy. It is tropic to androgen receptors and acts like testosterone, causing accelerated growth of muscle tissue, increases sex drive and endurance. Horny Goat Weed extract has antioxidant, antidepressant and nootropic effects.

Male bee brood (male bee-brood homogenate) is a natural substance which contains natural testosteroids, progesterone and estradiol. Male bee brood restores metabolism and nutrition of tissues, helps stabilize blood pressure, has a regulating effect on the tone of the vascular system and the level of blood circulation, lowers blood cholesterol level. It promotes the accelerated recovery of biochemical and massmetric characteristics of testes and prostate. As a stimulant of the central mechanisms of regulation of androgen formation, it increases physical performance, helps restore impaired sexual function in males and increase sexual desire.

Pollen or beebread are male plant cells, a natural concentrate containing proteins, all essential amino acids, carbohydrates, lipids, minerals and microelements (potassium, calcium, phosphorus, iron, magnesium, manganese, chromium, zinc, iodine, etc.), vitamins (carotenoids, C, D, E, groups B, P, PP, K, et al.), phytohormones and flavonoids. Pollen restores liver function, lowers the level of blood sugar, normalizes the process of digestion; stimulates the adrenal glands, lowers blood cholesterol; normalizes blood pressure; increases stress resistance, mental and physical performance.

Zinc citrate—zinc has a strong immunostimulatory effect. It actively influences the state of the sexual function in men: it is a building material for testosterone, increases activity of sperm cells, promotes proper functioning of male sex glands. Zinc deficiency plays a key role in the development of benign prostatic hyperplasia (adenoma) (BPH) where the activation of the 5-alpha-reductase enzyme occurs, which converts testosterone into dihydrotestosterone (DHT). The level of testosterone in blood decreases, DHT accumulates in the prostate gland which leads to prostate enlargement. Whereas high content of zinc contributes to blocking this process. It has psychotropic (improves mood, reduces irritability, improves memory and attention) and antioxidant actions. Zinc citrate is available as dihydrate and trihydrate and is produced by complete neutralization of citric acid with a high purity zinc source, subsequent precipitation and dehydration.

Vitamin $B_6$ normalizes hormonal balance, enhances immunity, improves the heart function, restores the function of prostate cells. It plays a significant role in the treatment of infertility and in energy processes occurring in spermatozoa, especially where their mobility is reduced.

True or false *ginseng* root has adaptogenic, bio-stimulating, and tonic effects. Its pharmacological activity results from having saponin glycosides and ginsenoides, fatty and ester oils, sterols, peptides, vitamins and minerals. The active ingredients of *ginseng* improve prostate function and sexual activity, actively influence the central nervous system, increase working capacity, and reduce physical and mental fatigue. In addition, *ginseng* improves the functional activity of cardiovascular system and regulates blood pressure.

*Leuzea* root has tonic and stimulant properties. The main pharmacological properties are the increase of muscle strength and performance, improvement of blood supply to muscles and brain. On long-term ingestion, it reduces morbidity, improves self-reported health, increases static endurance, improves mental and physical performance.

As one could see, none of the proposed components of the proposed composition has a pronounced effect on the libido increase. Any two, three, four or five components of the proposed composition do not substantially increase libido either.

It was established during research that only the combination of those components and only in that range can significantly increase libido, by 20-43% which is sufficient to amount to significantly more than the judicial exception and to make it protectable in terms of 35 U.S.C. §101. In other words, the tests revealed features sufficient to produce the desired synergistic effect.

Increasing libido even by 20% is significant as not all known drugs that enhance sexual activity can increase libido even up to 20%.

The libido level is a determining factor in male sexual activity, potency preservation, physiological and mental health.

In the study of "Remedy 1", significant improvement of neurohumoral and mental components of the male copulative cycle was revealed resulting in the enhancement/restoration of libido and overall satisfaction with sexual relations in the studied males.

A positive correlation was established between the increase of androgen concentration in blood (for total testosterone and dehydroepiandrosterone sulfate) and a significant libido increase (by 42.8%) in men which indicates that the preparation has a central hypothalamic-pituitary mechanism of action. It is assumed that androgens enhance desire by increasing the sensitivity of the pleasure centers in the limbic system and hypothalamus, as well as by increasing overall activity and vitality of the body due to the stimulating effect of androgens on metabolism.

The central mechanism of action of the preparation is confirmed by the decrease of prolactin level in blood serum (from 548±136 to 24.5-467 mU/l, $p<0.02$) and the demonstration of anti-stress, psycho-stabilizing effects, as well as by the increase of libido, sexual activity due to the stimulating action of LH on Leydig cells secreting testosterone.

The claimed supplement is made in powder, tableted or capsuled forms and may also have a form of alcohol water extract and forms based on such an extract, namely, powder, tablets and capsules.

EXAMPLES OF FOOD SUPPLEMENT PREPARATIONS

Example 1

For 1000 packages in capsules of 0.5 g with 100 capsules per package, provided is a 50 kg mixture of powdered pollen (5000 g), L-arginine (15000 g), male bee-brood homogenate (5000 g), zinc citrate (1000 g), icariin (Horny Goat Weed extract) (5000 g), Vitamin $B_6$ (30 g), true *Ginseng* root (4500 g), *Leuzea* root (2500 g), and fillers (lactose) (11970 g). The mixture is stirred in a mixer for 3 hours, and then it is encapsulated in a known manner.

Example 2

For 2000 packages in tablets of 0.5 g with 100 tablets per package, provided is a 100 kg mixture of powdered pollen (10000 g), L-arginine (30000 g), male bee-brood homogenate (10000 g), zinc citrate (2000 g), icariin (Horny Goat Weed extract) (10000 g), Vitamin $B_6$ (60 g), true *Ginseng* root (9000 g), *Leuzea* root (5000 g), and fillers (lactose) (23940 g). The mixture is stirred in a mixer for 3 hours; then it is tableted in a known manner.

The above-identified technical result is confirmed by researches conducted in the "Secrets of Longevity" medical center in Penza, which showed high efficiency of the claimed preparation with regard to the libido increase as compared to control groups.

Prepared for the first study were six-component food supplements based on Horny Goat Weed—Remedy 1 and on *Leuzea*—Remedy 2. The following compounds in a daily dosage were suggested for the study:

Contents of Components in the "Remedy 1":

| Components | mg |
|---|---|
| L-Arginine | 900 |
| Icariin from Horny goat weed | 60 |
| Decenoic acids from male bee brood | 1 |
| Rutin from pollen or beebread | 48 |
| Zinc from zinc citrate | 9 |
| Vitamin $B_6$ | 1.8 |

Contents of Components in the "Remedy 2":

| Components | mg |
|---|---|
| L-Arginine | 900 |
| Ecdysteroids from Leuzea root | 0.15 |
| Decenoic acids from male bee brood | 1 |
| Rutin from pollen or beebread | 48 |
| Zinc from zinc citrate | 9 |
| Vitamin $B_6$ | 1.8 |

The study investigated the clinical peculiarities of psychogenic erectile disorders and associated mental disorders, it estimated the efficacy of "Remedy 1" and "Remedy 2" as for the sexual function by dynamics of blood testosterone level, as for sexual activity parameters (libido and erection) and psycho-emotional status in patients with erectile dysfunction; therapeutic dynamics of the remedies was also compared.

The clinical study was conducted on 30 men with erectile dysfunction. Inclusion criteria were: 19-60 years old (the age limit was associated with frequent detection of the pronounced cerebral organic and somatic pathology and involutional processes in men beyond 60); matching of patient's condition at the time of the inclusion to diagnostic criteria of ICD-10 for F52.2—absence of genital response, accompanied by one of the following neurotic disorders: anxiety-phobic (F40); mixed anxiety-depressive disorder (F41.2) and adaptation disorder (F43.2); and absence of leading organic pathology in the sexual disorder pathogenesis.

The study did not include patients with alcoholism, drug addiction, anatomical deformity of the penis, proven endocrine causes of ED, decompensated somatic diseases, and those using other treatment agents for ED and drugs that can cause ED.

All patients gave an informed consent to participate in the study.

To achieve the objectives of the study, patients were divided into 3 treatment groups—two experimental ones and a control one—by simple randomization technique: Group 1—Experimental group—12 people with erectile dysfunction and associated psycho-emotional disorders—to receive "Remedy 1" and the traditional psycho-pharmacotherapy; Group 2—Experimental group—13 people with erectile dysfunction and combined psycho-emotional disorders—to receive "Remedy 2" and traditional psycho-pharmacotherapy; and Group 3—Control group—5 people with erectile dysfunction and combined psycho-emotional disorders—to receive traditional psycho-pharmacotherapy.

During clinical and sexual examination, the pronouncement and dynamics of sexopathological symptoms on the background of therapy were evaluated according to the clinical questionnaire "Sexual Formula for Men" (SFM) and the sexual function status questionnaire (Vakina T. N., *Sexually-endocrinal function and lipid level in patients with cardiovascular pathology*, Ph.D. Medicine thesis, Saratov, 2001).

Laboratory and instrumental examination included complete blood count, urinalysis, hormonal status examination—the level of total serum testosterone, as well as transrectal ultrasound examination (TRUSE) of the prostate. Used was data of a consultative urologist examination.

The mental state of the patients was determined by a clinical and psychopathological method. Examination of personality characteristics was performed by using a Mini-Mult questionnaire. The pronouncement and dynamics of anxiety-depressive disorder symptoms during therapy were evaluated by the Hospital Anxiety and Depression Scale (HADS).

Registration of side effects was conducted on the UKU scale with the date of their onset and end.

The regimen of examination is presented in Table 1. During 4 weeks, "Remedy 1" and "Remedy 2" were administrated within daily dose 2 times a day 30 minutes before meal. The evaluation of the therapy results was performed on the 28th day of the treatment. The main criterion of efficacy was the recovery of sexual activity.

TABLE 1

The patient examination regimen

| Documents and examination methods | Stage 1, enrollment in the study Screening and randomization (0-7 days) | Stage 2, therapy by the supplement Days of treatment | | | | |
|---|---|---|---|---|---|---|
| | | 3 | 7 | 14 | 21 | 28 |
| Informed consent to examination participation | V | — | — | — | — | — |
| Case record form | V | V | V | V | V | V |
| SFM | V | — | — | — | — | V |
| Sexual function status questionnaire | V | — | — | — | — | V |
| Total serum testosterone level | V | — | — | — | — | V |
| HADS scale | V | — | — | — | — | V |
| Mini-Mult questionnaire | V | — | — | — | — | — |
| TRUSE of prostate | V | — | — | — | — | — |

TABLE 1-continued

The patient examination regimen

| Documents and examination methods | Stage 1, enrollment in the study Screening and randomization (0-7 days) | Stage 2, therapy by the supplement Days of treatment | | | | |
|---|---|---|---|---|---|---|
| | | 3 | 7 | 14 | 21 | 28 |
| Consultation of urologist | V | — | — | — | — | — |
| Blood and urine tests | V | — | — | — | — | — |
| Side effect evaluation | — | V | V | V | V | V |

The examination results were processed using the statistical program "STATISTICA-6.0". All 30 patients completed the study. Characteristics of patients with erectile dysfunction included in the study are presented in Table 2.

TABLE 2

Profile of the examined patients (n = 30) with erectile dysfunction

| Criteria | Patients treated by Remedy 1 (n = 12) | Patients treated by Remedy 2 (n = 13) | Control group patients (n = 5) |
|---|---|---|---|
| Age (average) | 49.6 ± 6.9 | 47.3 ± 5.9 | 47.3 ± 5.1 |
| Marital status | | | |
| Single | — | 4.8% | — |
| Married | 83.4% | 80.9% | 80.0% |
| Divorced | 8.3% | 4.8% | — |
| Civil marriage | 8.3% | 9.5% | 20.0% |
| Education | | | |
| Graduate degree | 58.3% | 57.2% | 60.0% |
| College degree | 16.7% | 19.0% | 20.0% |
| High school | 25.0% | 23.8% | 20.0% |
| Antropometric parameters | | | |
| Height to leg length ratio | 1.9 ± 0.03 | 1.9 ± 0.04 | 1.9 ± 0.02 |
| Body mass index | 25.9 ± 1.9 | 24.9 ± 1.9 | 25.0 ± 1.2 |
| Age at the onset of the disease (average) | 45.0 ± 5.3 | 44.2 ± 5.1 | 43.6 ± 4.9 |
| Duration of the disease (average) | 5.2 | 6.7 | 4.8 |
| Whether the treatment was given (yes, no, number) | yes - 1, no - 11 | yes - 3, no - 10 | no - 5 |
| Comorbid psycho-pathologic disorders | | | |
| Phobic anxiety | 41.6% | 46.1% | 40.0% |
| Anxiodepressive | 33.3% | 30.8% | 40.0% |
| Deadaptation | 25.1% | 23.1% | 20.0% |
| Somatic disease: | | | |
| CVD | 33.3% | 38.4% | 20.0% |
| Diabetes | 8.3% | 7.6% | — |
| Smoking | 41.6% | 46.5% | 40.0% |
| GIT | 33.3% | 30.7% | 40.0% |
| Prostate | 41.6% | 30.7% | — |

As far as patient clinical characteristics are concerned (at the treatment onset with "Remedy 1" and "Remedy 2"), no significant differences in the experimental and control groups were determined.

The average age of the patients was 48.1±6.0 years, the average duration of erectile disorder—5.6±2.7 years. Males with graduate degree (58.5%) dominated. By family status, patients were mostly married (81.4%). Most of the patients had weak (20%) and a weakened type of the average sexual constitution (55%).

When assessing risk factors, smoking was detected in 42.7%, increased body mass index—in 53.3%, cardiovascular diseases (with a history of hypertension, ischemic heart disease) were observed in 30.6% of patients.

According to the results of clinical and psychopathological examination, anxiety-phobic disorder was diagnosed in 42.6%, mixed anxiety-depressive disorder—34.7%, adaptation disorder—in 22.7% patients. The analysis of test results by Mini-Mult scale showed high levels of hypochondria in 86.7%, depression—54.3%, psychasthenia—52.7% patients. Average scores on the scales of hypochondria were 62 points, for psychasthenia—57 points, for depression—53 points, and schizoid type—51 points.

Sexual dysfunction in all patients included in the examination manifested as difficulty in the onset or maintaining erection sufficient for satisfactory sexual intercourse, in the absence of evident signs of organic pathology of sexual sphere, corresponding to ICD-10, "the lack of genital response" (F52.2).

Against the background of the therapy with "Remedy 1" and "Remedy 2" in the experimental groups, it was as early as on the 7th day of treatment that patients reported a subjective improvement in mood, increased self-esteem and confidence in their sexual opportunities, reducing tension and conflicts in family relationship, as well as increased frequency of spontaneous erections.

The analysis of the efficacy of "Remedy 1" and "Remedy 2" on sexual function of patients given clinical and dynamic changes in the testosterone level in blood revealed the following (Table 3):

TABLE 3

Dynamics of testosterone level at the background of the therapy

| Parameters studied | Average cumulative factors | | | | | |
|---|---|---|---|---|---|---|
| | $1^{st}$ group (n = 12) | | $2^{nd}$ group (n = 13) | | $3^{rd}$ group (n = 5) | |
| | before | at $28^{th}$ day | before | at $28^{th}$ day | before | at $28^{th}$ day |
| Total testosteron | 11.8 ± 4.4 | 14.6 ± 5.2 | 14.5 ± 4.7 | 17.3 ± 5.6 | 12.9 ± 4.7 | 13.1 ± 5.8 |

In group 1, where "Remedy 1" was used, testosterone levels increased by 23.7%, in the $2^{nd}$ group with "Remedy 2"—by 19.8%.

The growth of sexual activity indicators—libido and erection—with the use of "Remedy 1" and "Remedy 2" was detected by the Day 28 of therapy in 66.7 and 61.5% patients, respectively, the average increase of libido being 28.0 and 24.3% and erection—21.4 and 17.8%, respectively. The dynamic changes of sexual activity indicators (libido and erection) and psycho-emotional state of patients with erectile dysfunction and comorbid anxiety-depressive disorders are presented in Table 4.

| Components | Mg of active substance |
| --- | --- |
| Saponins from true or false ginseng roots | 9 |
| Ecdysteroids from Leuzea root | 0.15 |
| L-arginine | 900 |
| Icariin from Horny goat weed | 60 |
| Decenoic acids from male bee brood | 0.6 |
| Rutin from pollen or beebread | 48 |
| Zinc from zinc citrate | 9 |
| Vitamin $B_6$ | 1.8 |

TABLE 4

Results of therapy and performed tests as of $28^{th}$ day

| Examined parameters | $1^{st}$ group | | $2^{nd}$ group | | $3^{rd}$ group | |
| --- | --- | --- | --- | --- | --- | --- |
| | before | at $28^{th}$ day | before | at $28^{th}$ day | before | at $28^{th}$ day |
| SFM questionn. Sexual function status questionn. | 18.8 ± 3.2 | 21.9 ± 3.5* | 18.4 ± 3.1 | 21.4 ± 3.2* | 18.9 ± 2.1 | 19.1 ± 2.5 |
| Libido | 2.8 | 3.6 | 2.7 | 3.4 | 2.9 | 3.0 |
| Erection | 3.0 | 3.6 | 2.9 | 3.4 | 3.0 | 3.0 |
| HADS scale | | | | | | |
| Anxiety | 11.2 ± 0.8 | 6.9 ± 0.5** | 10.9 ± 1.0 | 7.1 ± 0.5** | 11.4 ± 0.3 | 8.5 ± 0.5 |
| Depression | 9.1 ± 0.4 | 6.2 ± 0.3* | 9.5 ± 0.7 | 6.1 ± 0.3* | 10.0 ± 0.4 | 7.9 ± 0.8 |
| Clinical effect Abs. | | 8 | | 8 | | 1 |
| Clinical effect % | | 66.7 | | 61.5 | | 20.0 |

Note:
*$p < 0.05$,
**$p < 0.001$

The therapeutic effect of the supplements was more pronounced in relatively young men in the absence of the above mentioned risk factors and pronounced anxiety-depressive psychopathologic disorders. It is shown by evidence of the effectiveness of the supplement in the treatment of erectile dysfunction in 75.2% of cases in men under 40.

The claimed preparation, a combined biologically active supplement based on L-arginine, icariin (*Rhaponticum carthamoides* extract), male bee brood, pollen (bee pollen), zinc citrate, and vitamin $B_6$, has the ability to increase sexual desire and improve the quality of erections and, therefore, is a vegetational alternative for the treatment of sexual disorders in male.

The use of "Remedy 1" showed an increase in the level of testosterone in the blood serum by 23.7%, "Remedy 1"—by 19.8% by the day 28 of treatment.

The improvement of indicators of sexual activity—libido and erection—and of psycho-emotional state with the use of the "Remedy 1" and "Remedy 2" treatment by the day 28 of treatment were detected in 66.7 and 61.5% patients, respectively. In the group of patients with "Remedy 1", average increase of libido and erection was by 28.0 and 21.4%, and in group 2—by 24.3 and 17.8%, respectively. There was a significant improvement of mental and emotional state, with the 50% reduction in the level of anxiety and depression in both the first and second groups of patients.

The second study was carried out with regard to all eight components of the supplement. The composition of "Remedy 3" in a daily dose was as follows:

Study objective: evaluation of the effectiveness of "Remedy 3" in the treatment of male sexual dysfunction.

The study explores clinical features of sexual dysfunctions in patients. The effectiveness of "Remedy 3" was evaluated by the dynamics of the level of testosterone, prolactin and dehydroepiandrosterone sulfate (DHEAS), and by the changes of the values of sexual functions (libido and erection) and psycho-emotional state of studied patients.

The study involved 10 men with sexual dysfunction (erectile dysfunction and decreased libido). The inclusion criteria were:

the age of 19-60 (the age disaggregation is in connection with frequent detection of the pronounced cerebral organic and somatic pathology, as well as involution processes in men over 65);

matching patient's condition at the time of inclusion to diagnostic criteria of ICD 10 for F52—sexual dysfunction (absence or loss of the sexual desire (F 52.0), absence of the genital response (F52.2)), accompanied by one of the following neurotic disorders: anxiety-phobic (F40); mixed anxiety-depressive disorder (F41.2) and adaptation disorder (F 43.2);

absence of leading organic pathology in pathogenesis of the sexual disorder.

The study did not include patients with alcoholism, drug addiction, anatomical deformity of the penis, decompensated somatic diseases, with the use of other treatment agents for ED and drugs that can cause ED.

It was an unblinded study, without a placebo control.

During clinical and sexologic examination, the pronouncement and dynamics of sexopathological symptoms during therapy were evaluated by a clinical questionnaire "Sexual Formula for Men" (SFM), an IIEF-5 questionnaire (International Index of Erectile Function), scale of assessment of sexual function (Vakina T. N. 2001, ibid.)

A laboratory and instrumental examinations included a complete blood count, a urinalysis, a quantitative determination of hormone content in blood serum as to total testosterone, prolactin and DHEAS by enzyme-linked immunosorbent assay, as well as a transrectal prostate ultrasound examination. Also used was urologist consultative examination data.

The mental state of the patients was determined by clinical and psychopathological method. Examination of personality characteristics was performed using Mini-Mult questionnaire. Pronouncement and dynamics of anxiety-depressive disorder symptoms during therapy were evaluated with the use of the Hospital Anxiety and Depression Scale (HADS).

The research was conducted as follows (Table 5): a preliminary study—1 week (checking the inclusion and exclusion criteria, obtaining consent to participate in the study, collecting medical history, assessing the general condition of organs and systems, conducting laboratory tests, clinical sexological and psychological testing). A phase of treatment—using "Remedy 3" at a dose of 2 tablets 3 times a day 30 minutes before meals for 4 weeks with the registration of changes in the general condition of the patient and side effects. A final evaluation of the treatment was carried on the 28-30 day with the assessment by the SFM questionnaire, scale of assessment of sexual function, hormonal tests, HADS scale, identification of the preparation acceptability.

TABLE 5

Patient examination regimen

| Documents and research methods | Stage I (enrollment) Screening and randomization (0-7 days) | Stage II (therapy using 'Remedy 3" Days of treatment | | | | |
|---|---|---|---|---|---|---|
| | | 3 | 7 | 14 | 21 | 28 |
| Informed consent to the participation | V | — | — | — | — | — |
| CRF | V | V | V | V | V | V |
| CFM questionnaire | V | — | — | — | — | V |
| IIEF-5 questionnaire | V | — | — | — | — | V |
| Sexual function state scale | V | — | — | — | — | V |
| Total testosterone, prolactin, DHEAS level in blood serum | V | — | — | — | — | V |
| HADS scale | V | — | — | — | — | V |
| Mini-Mult questionnaire | V | — | — | — | — | — |
| TRUS of prostate | V | — | — | — | — | — |
| Consultation of urologist | V | — | — | — | — | — |
| Blood and urine tests | V | — | — | — | — | V |
| Evaluation of side effects | — | V | V | V | V | V |

Effectiveness evaluation was based on the dynamics of indicators of the scale of assessment of sexual function, the "Sexual Formula for Men" (SFM) questionnaire, HADS scale, the results of hormone tests, and evaluation of the clinical effectiveness of the therapy by a physician.

When assessing the clinical efficacy by the patient, the end result was defined as excellent (no complaints, resumption of sexual activity in full extent), good (considerable improvement, but still with some complaints), satisfactory (the patient noted improvement, but full recovery of sexual activity did not occur), with no effect.

The results were processed using the "STATISCTICA-6.0" statistical program.

According to the results of the study, all 10 patients completed the study. General characteristics of the patients included in the study are presented in the Table 6.

TABLE 6

Personalities of examined patients with sexual dysfunctions (n = 10)

| Indices | Patients treated with EROMAX 3 (n = 10) |
|---|---|
| Age (average) | 46.9 ± 5.1 |
| Marital status | |
| Single | 10% |
| Married | 60% |
| Divorced | 30% |
| Civil union | — |
| Level of education | |
| Graduate | 80% |
| Undergraduate | 20% |
| High school | — |
| Anthropometric parameters | |
| Trochanteric index | 1.89 ± 0.04 |
| Body-weight index | 26.9 ± 2.9 |
| Age at the onset of disease (average) | 41.6 ± 6.0 |
| Duration of disease (average) | 4.9 ± 2.3 |
| Whether treatment was provided (yes, no) | Yes - 4, no - 6 |
| Comorbid psychopathological disorders: | |
| Anxiophobic | 10% |
| Mixed Anxiodepressive | 30% |
| Deadaptation | 60% |
| Somatic diseases: | |
| CVD | 70% |
| Diabetes | 10% |
| Smoking | 30% |
| GI diseases | 30% |
| Prostate diseases | 40% |

Average age of patients was 46.9±5.1, average duration of sexual disorders—4.9±2.3 years. Dominant (80%0 were men with the graduate level of education. By family status, patients were mostly married men (60%). The majority of the patients had weak (50%) and a weakened type of the average sexual constitution (30%).

The assessment of risk factors, smoking was detected in 30%, increased body-weight index—in 50%; cardiovascular diseases (hypertension, ischemic heart disease in history) were observed in 70% of patients.

Most of the patients had a history of significant mental and physical stress, and the clinical and psychopathological study revealed adaptation disorders in 60% patients. Analysis of test results on Mini-Mult scale showed high levels of hypochondria in 60%, depression—in 50%, psychasthenia—in 50% of patients. Average scores on a psychasthenia scale were 62.8 points, hypochondria—59.8 points, depression—52 points and hysteria—51 points.

Sexual dysfunction in all patients included in the study showed themselves as decreased libido with a decrease of sexual fantasies, search of sexual incentives, thoughts about the sexual side of life and difficulties in the onset of, or sustaining, erection sufficient for satisfactory sexual intercourse, with the absence of evident signs of organic pathology of the sexual sphere, accompanied by anxiety and depressive symptoms.

The main complaints of patients reflecting the clinic of androgen deficiency according to age groups are presented in Table 7.

TABLE 7

Patient main complaints characteristic for androgen deficiency clinical findings

| Symptoms | Age groups | |
|---|---|---|
| | Before 45 (n = 2) | Over 45 (n = 8) |
| Genitourinary disorders | | |
| libido lowering | 50% | 100% |
| erectile dysfunction | 100% | 75% |
| decrease in orgasm freshness | 50% | 75% |
| Vascular and autonomic dysfunction | | |
| sudden hyperemia of the face, neck | — | 37.5% |
| blood pressure fluctuations | — | 75% |
| cardialgia | — | 50% |
| dizziness | — | 25% |
| short-of-breath feeling | — | 37.5% |
| hyperhidrosis | — | 50% |
| Psycho-emotional disorders | | |
| hyperirritability | 100% | 75% |
| lowered ability to concentrate | — | 75% |
| cognitive and memory deterioration | 50% | 50% |
| depression | 50% | 50% |
| insomnia | — | 25% |
| "vital power" decreasing | | 75% |
| Somatic disorders | | |
| decrease in muscle mass and strength | — | 37.5% |
| adipose tissue build-up | — | 75% |
| osteoporosis | — | 12.5% |
| decreased skin tone and thickness (skin laxity) | — | 25% |

It is noteworthy that in the age group over 45 the decreased libido was observed in all patients (100%), the erectile dysfunction being present in 75% of the cases (Table 7).

The analysis of erectile dysfunction according to the IIEF-5 scale showed that 1 patient (10%, 22 points) had a value within the normal range; mild erectile dysfunction was detected in 5 cases (50%, 18 points average), moderate ED—in 4 (40%, 14 points average).

Against the background of therapy by "Remedy 3," the majority of patients (60%) by the 5-7$^{th}$ day noted subjective improvement of mood, increased self-esteem and confidence in their sexual abilities, reducing tension and conflict situation in the family relationship, as well as increased frequency of nocturnal erections.

Studying the "Remedy 3" effectiveness on sexual function of patients taking into account clinical and dynamic changes in the level of testosterone, prolactin and dehydroepiandrosterone sulfate (DHEAS) in serum showed the following (Table 8):

TABLE 8

Dynamics of testosterone, prolactin and DHEAS level in serum in view of the therapy performed

| Parameters | Before treatment | As of 28$^{th}$ day of treatment | Normal values | p |
|---|---|---|---|---|
| Total testosterone | 11.8 ± 4.4 | 17.1 ± 5.7 | 12.1-38.3 nmol/L | <0.02 |
| Prolactin | 548 ± 136 | 285 ± 60 | 24.5-467 mU/L | <0.02 |
| DHEAS | 1.2 ± 0.3 | 1.4 ± 0.7 | 1.0-4.2 mcg/mL | >0.054 |

Against the background of the use of "Remedy 3", there were reliably elevated levels of total testosterone ($p<0.02$) and DHEAS against the lowered prolactin level ($p<0.02$) (the latter could also be regarded as anti-stress improving trends in the studied group of patients).

The testosterone level growth rate when using "Remedy 3" was 44.9%. These changes of hormonal status made it possible to reduce the number of patients' complaints on vegeto-vascular dysfunction—sudden hyperemia of face and/or neck, hyperhidrosis, short-of-breath feeling, fluctuations of blood pressure, as well as on psycho-emotional sphere. Patients reported mood stabilization, addition of "vital energy force", improvement of alertness, memory, normalization of sleep. The amount of adipose tissue decreased which revealed itself in a decrease of waist circumference by an average of 3.9 cm for 1 month.

At the time of the control evaluation—after 4 weeks of treatment—patients had significant change of factors on the scale of sexual function assessment: libido—4.0 points versus baseline of 2.8 ($p<0.02$), average increase of the libido was 42.8%, erection—3.8 points versus baseline of 2.9 ($p<0.032$), average increase of the erection factor was 31%.

When assessing the sexual function in accordance with the SFM questionnaire, revealed before treatment was a general decline of male copulation cycle values. Against the background of the therapy with "Remedy 3", the total score of male sexual function increased from 17.7±2.5 to 23.8±2.9 ($p<0.02$). Among the structural indicators of SFM, a mental component of the male copulation cycle improved more significantly that resulted in the increase of libido and overall satisfaction with sexual relations in the studied patients.

Consideration of dynamic changes of parameters of comorbid psycho-emotional disorders—anxiety and depression—in patients with sexual dysfunction showed that if before the treatment the average level of anxiety was regarded as a clinical one and was 11.5±0.6 points on HADS, it decreased after treatment to a normal level of 6.9±0.3 points ($p<0.02$). The average level of depression on the HADS scale at the beginning of treatment was approaching to clinical one—10.8±0.5 points; but by the checking 28$^{th}$ day the depression values were reduced to normal levels—6.7±0.3 ($p<0.02$).

During therapy with "Remedy 3" (from Day 2 to Day 4 of the treatment) three patients had transient diarrhea. It resolved aidlessly. Indicators of blood count, urinalysis, and biochemical blood tests were within the normal range before the start of treatment and at its end. Overall tolerability of "Remedy 3" was good.

When evaluating the clinical efficacy of the treatment, two (20%) patients evaluated results as "excellent"—no complaints, the resumption of sexual life in its entirety; six (60%) patients—as "good"—a considerable improvement, though some complaints remain; and two (20%)—as "satisfactory"—the patients noticed an improvement, but there occurred no full recovery of sexual activity. However, the latter ones had an improvement in the parameters of hormonal status with the higher levels of total testosterone and the decrease of prolactin.

Summing up, sexual dysfunction is common in patients with anxiety and depression and requires an adequate specific therapy. "Remedy 3" is a combined biologically active supplement that is based on L-arginine, *ginseng* root, *Leuzea* root, horny goat weed extract, pollen (beebread), zinc citrate, vitamin B6, and it is able to increase sexual desire and improve the quality of erection, and hence is a natural and safe alternative effective treatment for sexual dysfunction in males. The use of "Remedy 3" showed by day 28 of treatment a reliable increase of testosterone level (average increase of 44.9%) against the background of the prolactin level decrease, as well as a tendency to DHEAS increase. When using "Remedy 3", parameters of sexual activity—libido and erection —significantly changed: the average increase of libido was 42.8%, erection—31%. The therapy with "Remedy 3" led to stabilization of vegetative vascular system, as well as to significant improvement of mental and emotional state of patients with reducing anxiety and depressive disorders.

The invention claimed is:

1. A food supplement for restoring male sex drive, the composition comprising in a daily dose 300 to 1000 mg of L-arginine, 40 to 100 mg of rutin from pollen, 0.4 to 1.0 mg of decenic acids from male bee brood, 6 to 60 mg of zinc from a zinc compound, 0.3 to 3.0 mg of vitamin $B_6$, and 20 to 150 of icariin from horny goat weed.

2. A food supplement for restoring male sex drive, the composition comprising in a daily dose 300 to 1000 mg of L-arginine, 40 to 100 mg of rutin from pollen, 0.4 to 1.0 mg of decenic acids from male bee brood, 6 to 60 mg of zinc from a zinc compound, 0.3 to 3.0 mg of vitamin $B_6$, and 5 to 20 mg of saponins from *ginseng* root.

3. A food supplement for restoring male sex drive, the composition comprising in a daily dose 300 to 1000 mg of L-arginine, 40 to 100 mg of rutin from pollen, 0.4 to 1.0 mg of decenic acids from male bee brood, 6 to 60 mg of zinc from a zinc compound, 0.3 to 3.0 mg of vitamin $B_6$, and 0.1 to 30 mg of ecdysteroids from *Leuzea* or *Serratula coronata*.

4. A food supplement for restoring male sex drive, the composition comprising in a daily dose 300 to 1000 mg of L-arginine, 40 to 100 mg of rutin from pollen, 0.4 to 1.0 mg of decenic acids from male bee brood, 6 to 60 mg of zinc from a zinc compound, 0.3 to 3.0 mg of vitamin $B_6$, 5 to 20 mg of saponins from *ginseng* root, and 0.1 to 30 mg of ecdysteroids from *Leuzea* or *Serratula coronata*.

5. A food supplement for restoring male sex drive, the composition comprising in a daily dose 300 to 1000 mg of L-arginine, 40 to 100 mg of rutin from pollen, 0.4 to 1.0 mg of decenic acids from male bee brood, 6 to 60 mg of zinc from a zinc compound, 0.3 to 3.0 mg of vitamin $B_6$, 5 to 20 mg of saponins from *ginseng* root, and 20 to 150 of icariin from horny goat weed.

6. A food supplement for restoring male sex drive, the composition comprising in a daily dose 300 to 1000 mg of L-arginine, 40 to 100 mg of rutin from pollen, 0.4 to 1.0 mg of decenic acids from male bee brood, 6 to 60 mg of zinc from a zinc compound, 0.3 to 3.0 mg of vitamin $B_6$, 0.1 to 30 mg of ecdysteroids from *Leuzea* or *Serratula coronata*, and 20 to 150 of icariin from horny goat weed.

7. A food supplement for restoring male sex drive, the composition comprising in a daily dose 300 to 1000 mg of L-arginine, 40 to 100 mg of rutin from pollen, 0.4 to 1.0 mg of decenic acids from male bee brood, 6 to 60 mg of zinc from a zinc compound, 0.3 to 3.0 mg of vitamin $B_6$, 0.1 to 30 mg of ecdysteroids from *Leuzea* or *Serratula coronata*, 5 to 20 mg of saponins from *ginseng* root, and 20 to 150 of icariin from horny goat weed.

* * * * *